(12) United States Patent
Petersen et al.

(10) Patent No.: US 9,699,952 B2
(45) Date of Patent: Jul. 11, 2017

(54) SEED TESTING METHOD AND APPARATUS

(71) Applicant: Kamterter Products, LLC, Waverly, NE (US)

(72) Inventors: Christopher Lee Petersen, Lincoln, NE (US); John Alvin Eastin, Lincoln, NE (US); Timothy Raymond Meyer, Lincoln, NE (US)

(73) Assignee: Kamterter Products, LLC, Waverly, NE (US)

( * ) Notice: Subject to any disclaimer, the term of this patent is extended or adjusted under 35 U.S.C. 154(b) by 11 days.

(21) Appl. No.: 14/635,967

(22) Filed: Mar. 2, 2015

(65) Prior Publication Data
US 2015/0237792 A1    Aug. 27, 2015

Related U.S. Application Data

(60) Division of application No. 11/978,337, filed on Oct. 29, 2007, now Pat. No. 8,966,813, which is a continuation of application No. 11/903,022, filed on Sep. 20, 2007, now Pat. No. 8,375,628.

(51) Int. Cl.
*A01C 1/02* (2006.01)
*G01N 33/00* (2006.01)

(52) U.S. Cl.
CPC ......... *A01C 1/025* (2013.01); *G01N 33/0098* (2013.01)

(58) Field of Classification Search
CPC ......... A01C 1/025; A01C 1/06; A01C 21/005; G01N 33/0098; A01B 79/005; B65G 11/083; B65G 11/206
See application file for complete search history.

(56) References Cited

U.S. PATENT DOCUMENTS

| | | | |
|---|---|---|---|
| 1,007,050 A | 10/1911 | Bascom | |
| 2,867,946 A | 1/1959 | Kobs | |
| 4,135,331 A * | 1/1979 | Lamlee | A01G 31/02 206/815 |
| 4,236,350 A * | 12/1980 | Hasselbach, Sr. | A01G 9/16 47/17 |
| 4,291,494 A * | 9/1981 | Knablein | A01G 9/16 206/558 |
| 2006/0147340 A1 | 7/2006 | Yang et al. | |
| 2006/0218862 A1* | 10/2006 | Dyas | A01G 9/143 47/86 |
| 2006/0242895 A1* | 11/2006 | Winkler | A01G 9/16 47/17 |

* cited by examiner

*Primary Examiner* — Lisa J Hobbs
(74) *Attorney, Agent, or Firm* — Suiter Swantz pc llo

(57) ABSTRACT

To provide an accelerated aging seed testing kit system, a single sheet of plastic or other suitable formable sheet material is pressed into the shape of a compartment base having recesses for mounting a seed holder. A seed holder that includes a seed support and a seed support holder is formed. The seed support holder is formed of a single sheet of plastic having radially extending tabs that fit into the recesses of the container to support the seed support above the bottom of the test kit. A bypass channel for addition of an aqueous solution used in the prescribed test condition is provided in the seed holder. A lid is formed out of one piece of plastic having a bendable tab to serve as a port and the openings and connecting points of the lid and seed holder are positioned so they can only fit together in one orientation having the port above the bypass channel. The saturated cold germination test kit includes a compartment base, a lid and a holder for an oxygen scavenger. The base is water and airtight and includes a liquid gas exchange control trough around its perimeter. It is sized to house a high moisture holding seed planting surface pack at the bottom so seeds can be placed on top of the surface to imbibe and initiate pre-germination mechanisms. The lid has an edge that fits into a trough that houses a gas barrier liquid in the base to form an airtight seal and has an attachable compartment for an oxygen scavenger so the kit may be placed together in an airtight configuration with the oxygen scavenger inside to provide an anaerobic atmosphere for performing the saturated cold germination test in a cool location.

8 Claims, 9 Drawing Sheets

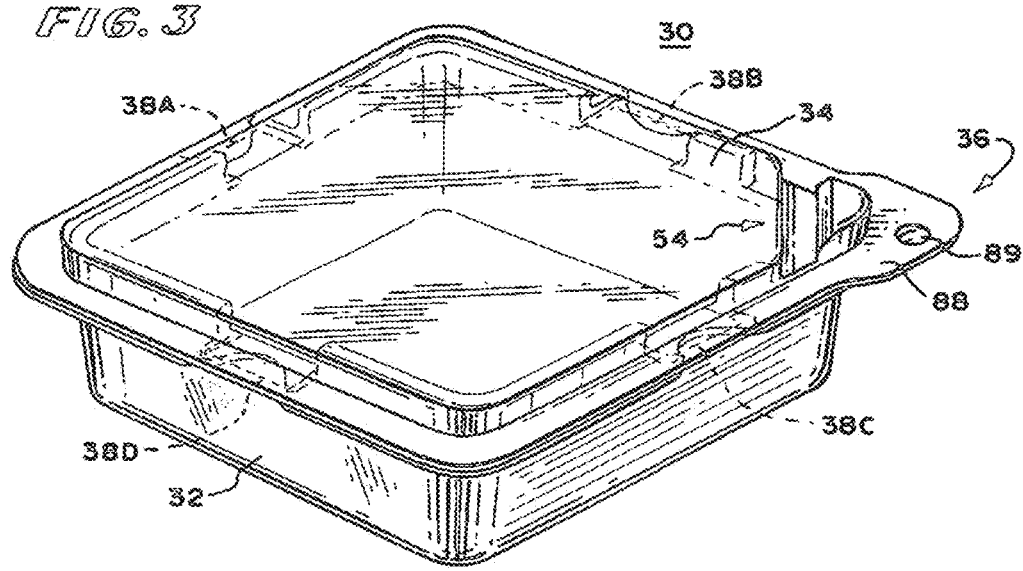
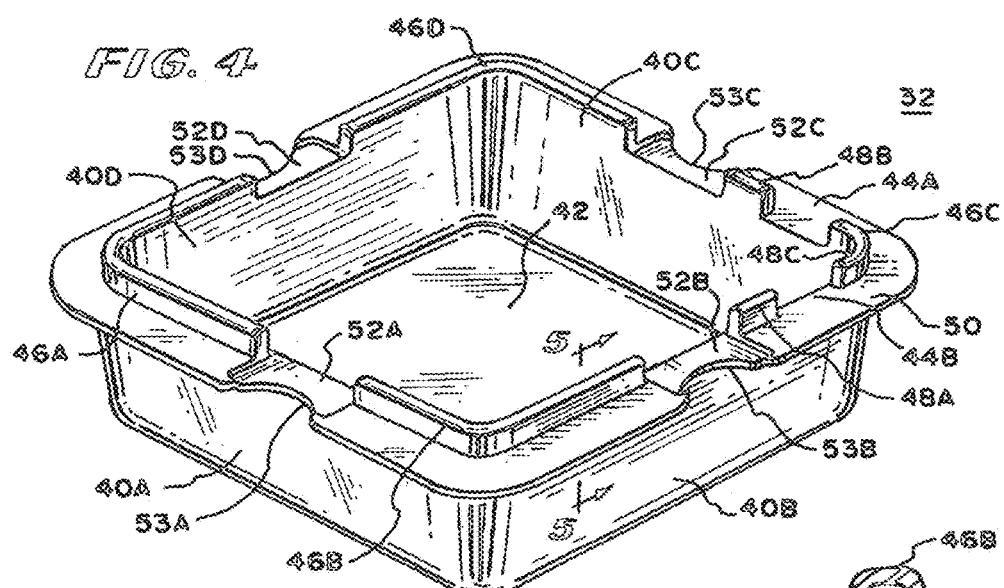
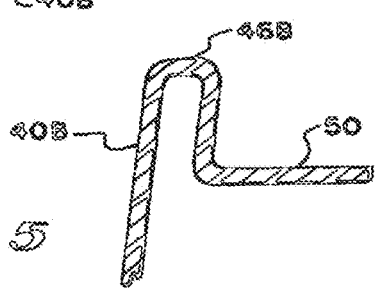

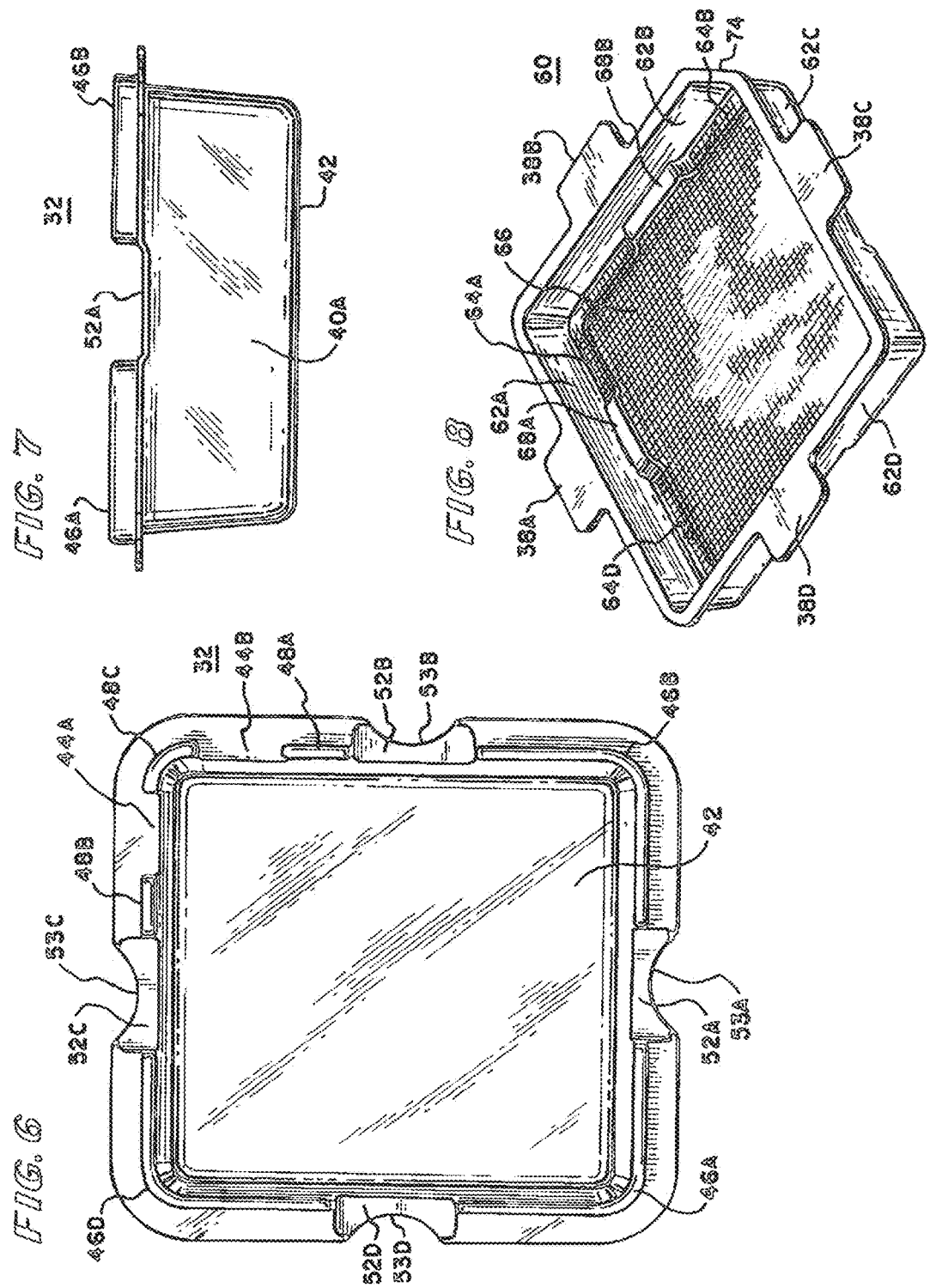

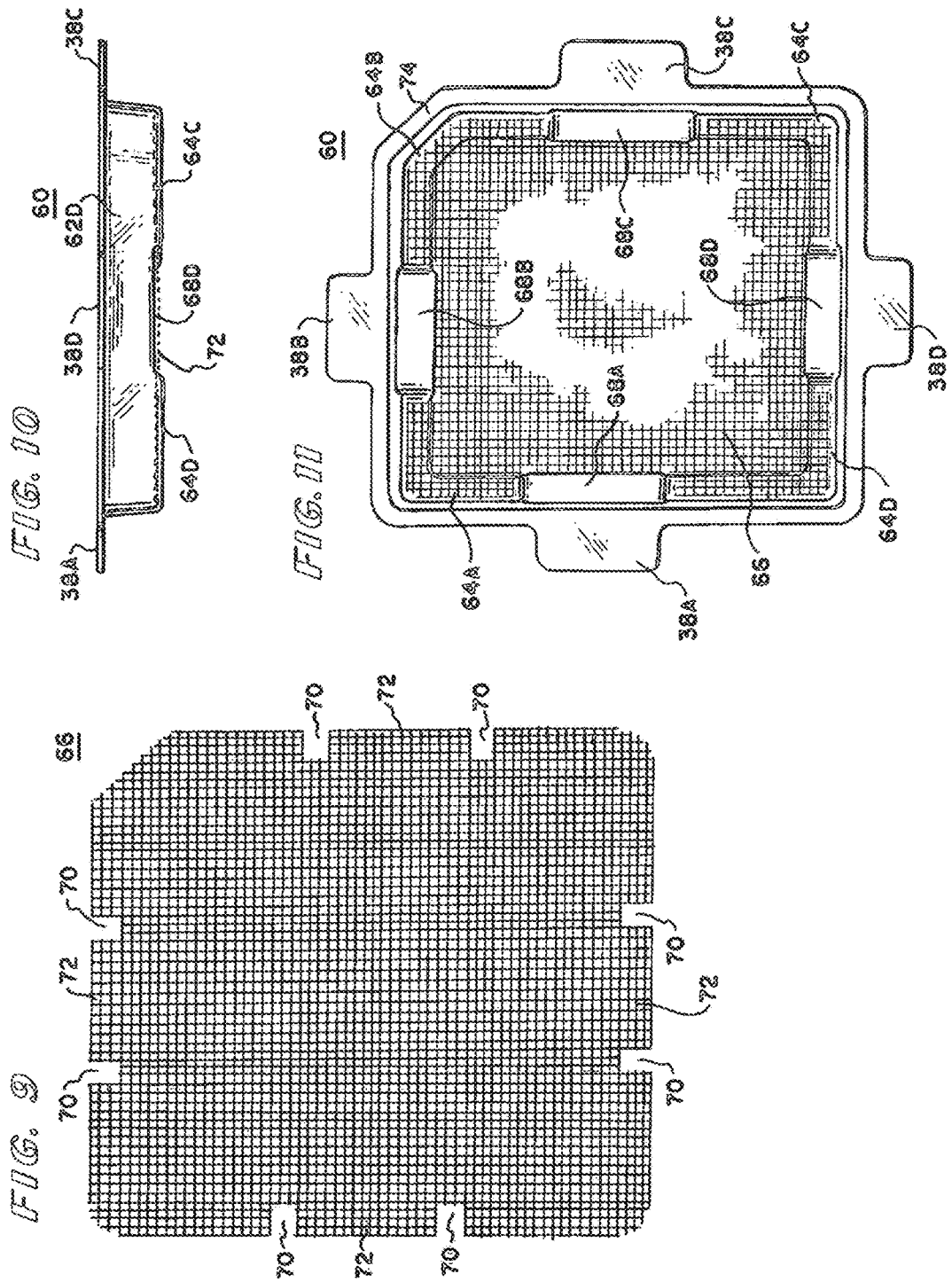

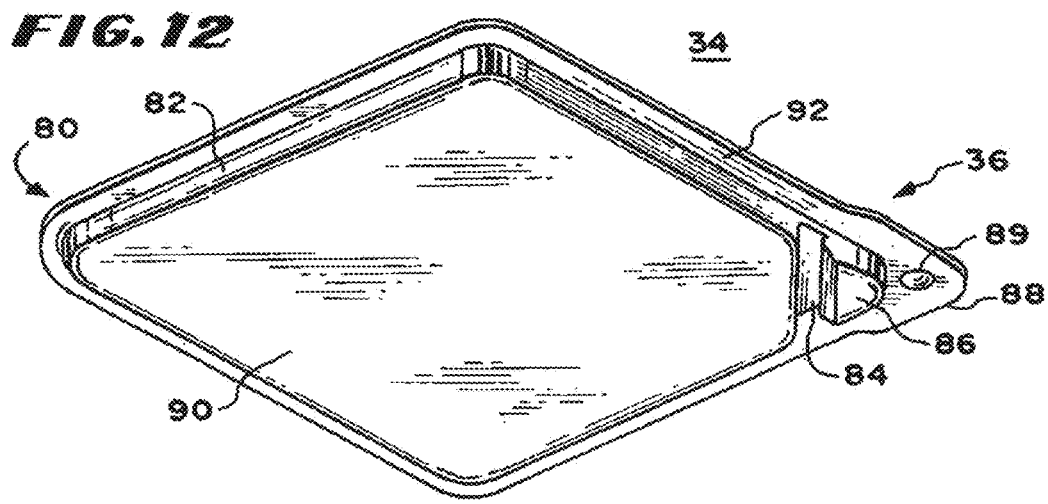
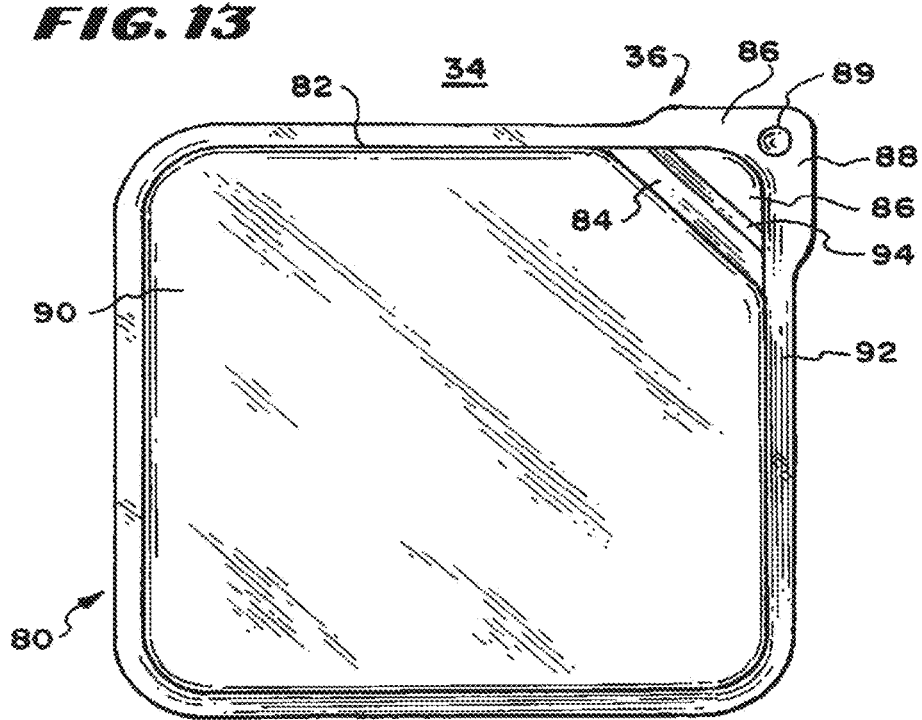

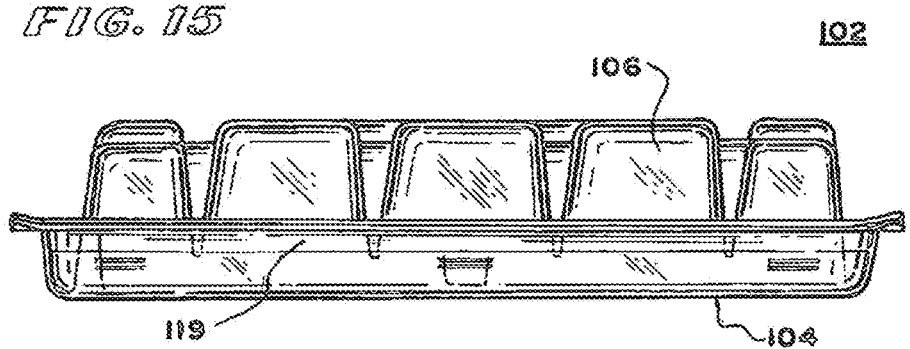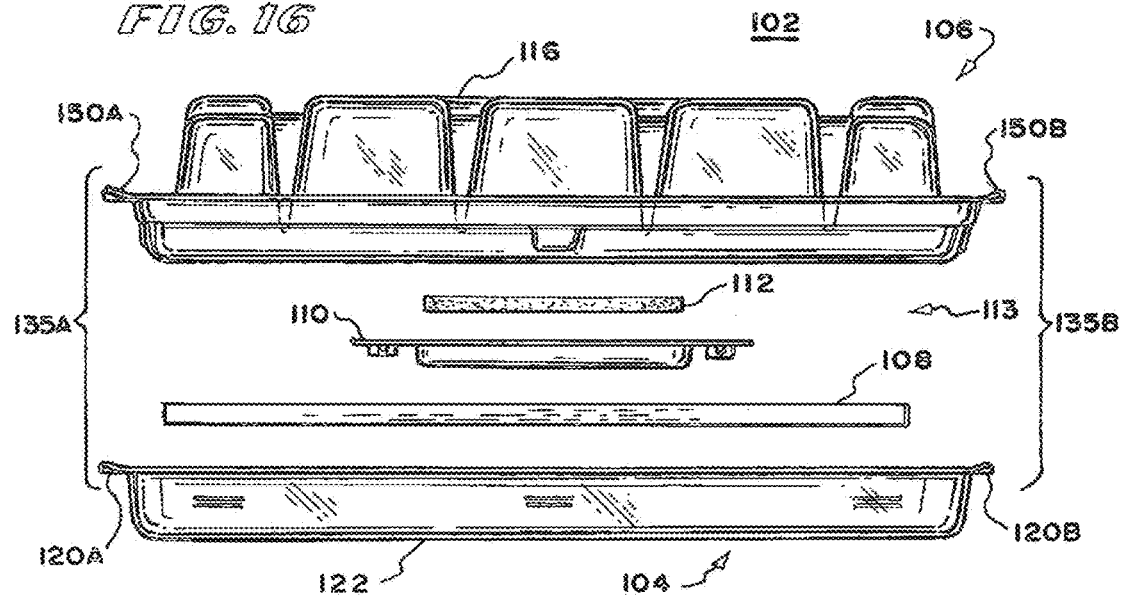

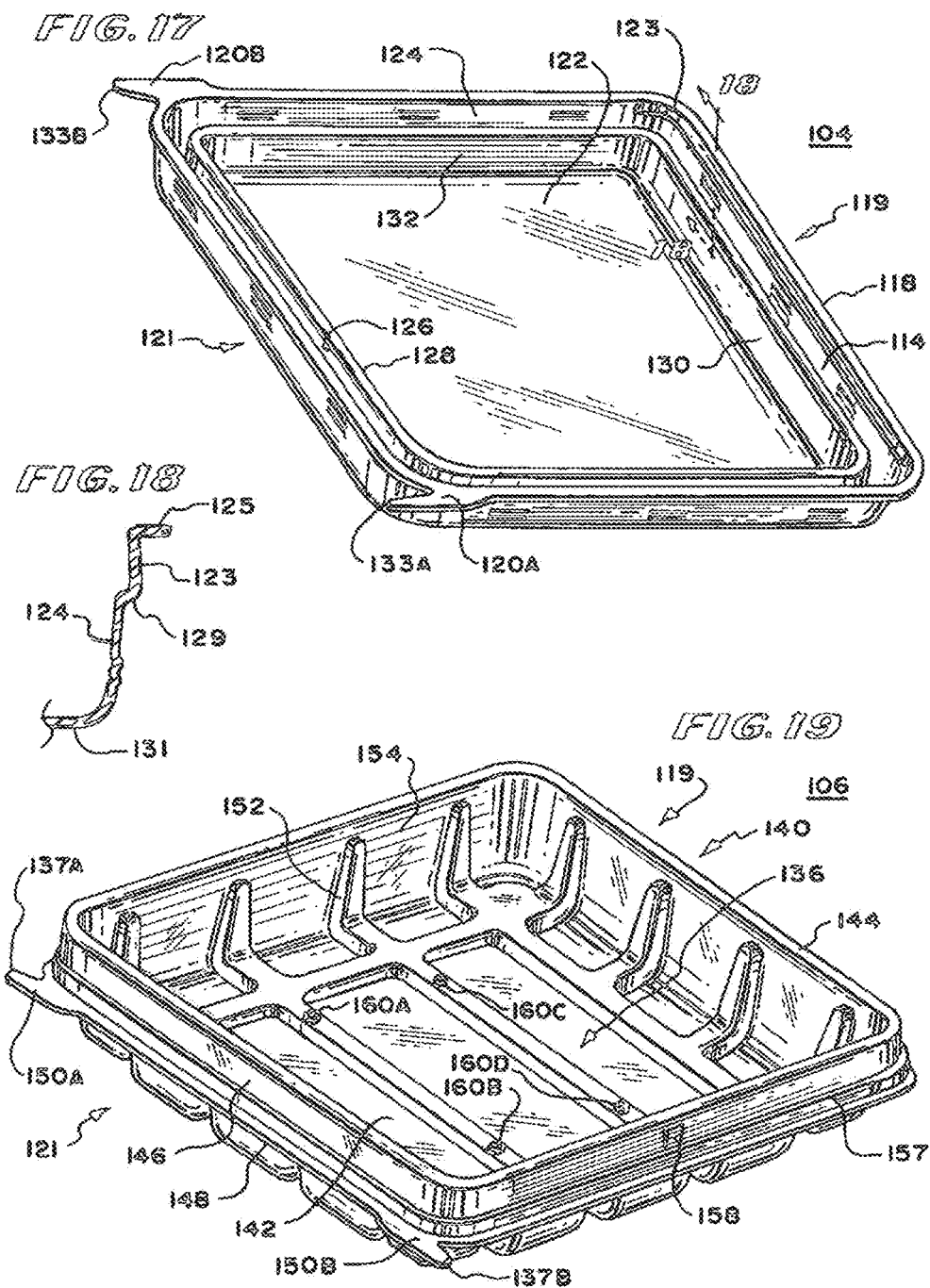

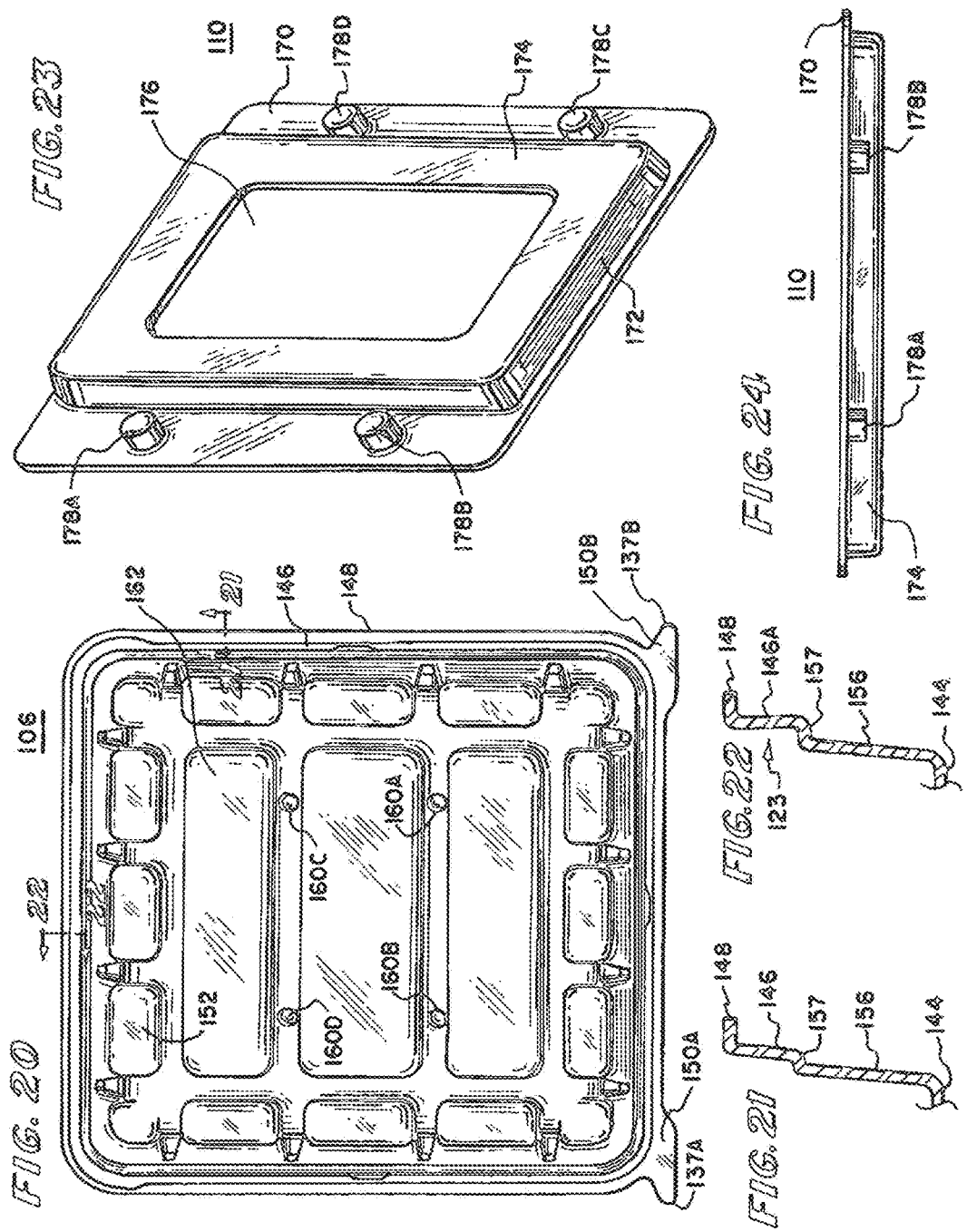

SEED TESTING METHOD AND APPARATUS

CROSS REFERENCE TO RELATED APPLICATIONS

This application is a divisional application of U.S. patent application Ser. No. 11/978,337 titled "SEED TESTING APPARATUS FOR ACCELERATED AGING", filed on Oct. 29, 2007. U.S. patent application Ser. No. 11/978,337 is a continuation of U.S. patent application Ser. No. 11/903,022, titled "SEED TESTING METHOD AND APPARATUS", filed on Sep. 20, 2007.

BACKGROUND OF THE INVENTION

This invention relates to seed testing.

It is known to test seeds to assess seed quality or viability or to predict performance of the seeds in the field. Generally, these tests are performed in accordance with the Association of Official Seed Analysts Rules (AOSA) or the International Rules for Seed Testing to provide repeatability for comparing different seed lots. The tests emphasize reliability, standardization, efficiency and cost.

For example, one known standardized test is referred to as an accelerated aging test. This test is used to predict the effects of storage on seeds as indicated by the percentage of healthy seedlings derived from seeds subjected to accelerated aging. Kits are commercially available for this test. In one accepted version of this test, seeds are suspended above water at a warm temperature for a period of time. The temperature and time may vary within species between hybrid or inbred lines and may vary from species to species. They are in accordance with accepted standards such as the International Rules for Seed Testing or the AOSA. After accelerated aging, the seeds are typically tested for viability by standard warm germination protocols.

Accelerated aging of seeds is conducted within an assembly comprised of a container, a lid for the container and a removable seed-holding tray that fits within the container. The tray includes a horizontal screen support for holding the seeds above water in the container. In use, prior to starting the test, several accelerated aging units are prepared. In preparing the units, water is dispensed into the container, the trays are placed in the containers and seeds are placed on the screens. The containers are marked and the test is started. The test is started by placing the closed containers, containing water, a seed-holding tray in which a screen is incorporated to suspend seeds above the water in the container, and seeds residing on top of the screen of the seed holding tray in an environment where the container or containers will have the desired incubation temperature.

In a prior art type of accelerated aging assembly, the tray includes posts, a screen support and the screen. The posts hold the screen and screen support at a height above the expected water level. The screen support includes vertical walls with a horizontal bottom ledge that receives the screen. It has been discovered that the prior art method and apparatus for performing accelerated aging tests can advantageously be improved in several ways, such as: (1) by reducing the cost of manufacture; (2) reducing the time required for performing the tests; (3) reducing the number of steps needed to perform the test and thus reducing the opportunities for error; and (4) reducing microbial cross contamination problems that existed in the prior art non-disposable test kits. The cross contamination problems with the prior art non-disposable test kits are an undesirably high likelihood of cross contamination between tests and the consequent effort needed in sterilizing the test-kit components between successive uses of the test kits for the prior art non-disposable test kits.

Another type of standardized test is known as a saturated cold germination test. This test is used to measure the ability of seeds to germinate in cold, high moisture and anaerobic soil environments and to assess the general vigor of seed lots. It is intended to simulate early season adverse field conditions. Standardized saturated cold test procedures are normally used. In one known version of this test, corn seeds are inserted with the embryo down on saturated soil and maintained at a low temperature for several days or for a prescribed period of time and then moved to a warm germination temperature. The test procedures for other species differ from corn and the temperature and time values for other species are provided by the International Rules for Seed Testing or the Association of Official Seed Analysts Rules. A typical saturated cold test assembly consists of water saturated paper, such as water saturated towels overlaid with loose soil. The seeds are inserted in the loose soil. The saturated cold test assembly is then maintained at a low temperature for a prescribed time period before being moved to a warm temperature to complete the test.

The prior art methods and apparatuses can benefit from improvements to reduce labor and time in the tests and to increase standardization and repeatability.

SUMMARY OF THE INVENTION

Accordingly, it is an object of the invention to provide a novel accelerated aging test kit.

It is a further object of the invention to provide a novel method for performing accelerated aging tests on seeds.

It is a further object of the invention to provide a novel test kit which is inexpensive to make and is disposable.

It is a still further object of the invention to provide a novel test kit that avoids microbial cross contamination.

It is a still further object of the invention to provide a novel test kit that avoids microbial cross contamination It is a still further object of the invention to provide a novel test kit that avoids microbial cross contamination by disposing of some or all of the test kit components rather than attempting to sterilize them.

It is a still further object of the invention to provide a novel test procedure for accelerated aging that may be performed with fewer steps and more reliability than existing accelerated aging tests.

It is a still further object of the invention to provide a novel saturated cold germination test procedure.

It is a still further object of the invention to provide a novel saturated cold germination test kit.

It is a still further object of the invention to provide a novel repeatable stress test that exposes the seeds to a stress-inducing atmosphere.

It is a still further object of the invention to provide a novel test procedure that reduces variability caused by non-standard components such as soil from different sampling sites.

It is a still further object of the invention to provide a novel test procedure that uses more standardized stress inducing conditions than can be achieved from current sources such as using moist soil selected inoculum.

It is a still further object of the invention to provide a novel test kit with a controlled exact and partial anaerobic environment.

It is a still further object of the invention to provide a novel method of performing saturated cold germination tests that correlate reliably with standard tests.

It is a still further object of the invention to provide a novel method of performing saturated cold germination tests that predict seed vigor.

It is a still further object of the invention to decrease the time duration of saturated cold test procedures.

It is a still further object of the invention to provide faster results and greater throughput in a saturated cold germination test.

It is a still further object of the invention to provide a saturated cold germination test kit that provides results with improved reproducibility.

It is a still further object of the invention to provide a test kit that permits easy standardization of tests.

It is a still further object of the invention to provide a test kit that does not require components such as soil that may produce variability from one test to another.

In accordance with the above and further objects of the invention, a test kit for accelerated aging tests of seeds includes single-walled components using a unitary body design and matching locators. In this specification, the term "single-walled component" means a component of a test kit formed from a continuous plastic or other formable sheet material having uniform thickness without portions at an angle to or parallel to other portions except where bent to the angle or bent to be parallel to another portion. The adjective "single-walled" before the name of a component means that component is formed from a continuous plastic or other formable sheet material having uniform thickness without portions at an angle to or parallel to another portion. Instead of a PVC plastic sheet, other formable plastic sheet material may be used. In this specification, the term, "formable sheet material" means a sheet of any suitable material that can be formed into the walls or shelves or closures of the test kits that are the subject of the embodiments of this invention. Generally they are inexpensive plastics that can be formed into the desired shape by conventional methods. In the preferred embodiment, one of the formable sheet materials is PVC, formed by pressure molding into component parts. However, another formable sheet material that can be used is an extruded plastic screen or woven wire screen. For example, the term formable sheet material includes cross members such as thin wires formed into a screen and extruded hydrophilic or hydrophobic members forming a screen that may be useful for some applications.

One of the single-walled components is a single-walled seed support holder such as a single-walled support that includes a seed support to support seeds. In the preferred embodiment the seed support is a screen. In this specification, the term "single-walled seed support" means a tubular seed holder for an accelerated aging test kit that includes a moisture passing member such as a screen that is adapted to support seeds and is held by a holder made of plastic or other formable sheet material. The moisture passing member has openings adjusted so that together with the seal on the container and the nature of the material of which the seed support is made the exposure to and partial pressure of moisture are established with sufficient reliability to maintain standards of aging capable of correlation with storage and with other protocols for accelerated aging. In the preferred embodiment, the single walled seed support holder is formed from a continuous single sheet of plastic or other formable sheet material without wall portions extending transverse to other wall portions other than edges where the transverse wall portions are bent. These transverse wall portions include: (1) one or more bends that support a seed holder which is held by friction within a horizontal support; and (2) either: (a) bent portions that include tabs supported by wall portions of the test kit housing; or (b) legs resting on the bottom of the test kit housing.

With this arrangement, the tubular seed support holder may be made of plastic or other formable sheet material of substantially the same thickness and may be formed by thermoforming, vacuum forming or pressure forming in modest quantities at low cost. Of course, any other forming process may be used such as injection molding, compression molding or the like. The container has a unitary body design formed of plastic or other formable sheet material of substantially the same thickness with curved and folded high-moment of inertia sections for added strength. It includes sections which are marked or structured that force proper location of the parts. In this specification, "unitary body design" means a design of seed test kit in which strength is obtained by curved portions that increase the moment of inertia rather than by increasing the thickness of the parts or by the selection of strong but more expensive materials. Similarly in this specification, "matching locators" means markings on and/or physical construction of parts of the seed treatment kit that aid in or force the parts to go together with a particular correct orientation.

The single-walled seed support, cover and container include matching locators which are markings or physical features that aid in or force the parts to go together with a particular correct orientation. This correct orientation is utilized for example to provide an openable port at one location in the cover which matches an opening in the single-walled seed support holder through which a liquid may be poured to a level below the screen. The liquid is usually water or an aqueous solution and serves the function of maintaining a vapor pressure that accelerates aging. The single-walled seed support holder fits within specific locations in the container to have one particular orientation and the lid similarly fits at only one location and has a tab at one end which may be easily elevated. A non-adhered seed support and seed support holder combination is used.

The seed support holder is tubular and includes folded over top and bottom ledges; one of the top and bottom ledges supporting a screen and the other supporting the seed support on the container. In the preferred embodiment, the bottom ledge supports the screen and has elevated portions so that the seed support may rest on the horizontal bottom ledge with a portion of it inserted in underneath the elevated portion and portions above the elevated portions to be held by friction. The top ledge has bent over tabs which fit within depressed portions at the upper rim of the container so that they rest from the upper rim of the container at only one specific location. Thus, the container, seed support holder and lid may be formed of inexpensive sheet plastic or other formable sheet material using inexpensive equipment such as thermoforming, vacuum forming or pressure forming equipment.

In the operation of the preferred embodiment, the seed holders are positioned within the test kits and a plurality of seeds positioned on each screen of the screen holders. The test kits may be marked for identification. The lid may be placed on them and the end of the lid lifted to expose a port. The seed holder underneath the port has an opening through which an aqueous solution may be poured to a location below the seed support. When this is done, the test kit with the seeds in it is located at a warm temperature to accelerate aging. Under these warm and humid conditions, seed deterioration as a function of pathogen growth and/or seed metabolic processes may take place. Seed performance following accelerated aging is an indication of storage stability and vigor characteristics of the seed lot.

A saturated cold germination kit includes a container base, a source of moisture, a stress inducing atmosphere and a lid. The container includes an air seal. Advantageously, the source of moisture is water soaked-paper which may be located in the bottom of the container base and supports the seeds. However, other suitable water supporting media may be used. Preferably, the seeds are placed with the germ in or on the paper. While water soaked paper, a paper soaked in an aqueous solution, is inexpensive and can provide a standardized source, other materials may be used to provide a standardized saturated media surrounding the seed germ. To reduce the time needed to position the seeds uniformly with the seed germ in contact with a high concentration of an aqueous solution but with sufficient air for survival, inert particles or other media may be used to cover the seeds and permit air and moisture to be spread uniformly over each seed regardless of the orientation of the seeds.

Conveniently, the air seal is a liquid-filled groove in the container base that receives an edge of the container lid and the stress-inducing atmosphere is an atmosphere with reduced oxygen content. The liquid filled groove may contain an aqueous solution or any other material that flows and forms a seal. In this connection, the word "liquid" in this specification includes semi-liquid or malleable materials or materials that are liquid when poured into the trough but harden such as wax. Advantageously, the liquid that is used resists evaporation. To prevent the lid from floating from the base and thus breaking the air seal, an edge on a first side of the lid grips an edge of a corresponding first side of the container base to form a hinge-like structure and at least one other edge of a second side of the lid includes a fastener part that can be easily fastened to a corresponding fastener part on one other edge of a corresponding second side of the container base.

In the preferred embodiment, the reduced oxygen content is obtained by incorporating an oxygen scavenger in a compartment within the container attached to the lid. The liquid in the groove is a barrier to air and thus prevents oxygen from being transported into the container. In this manner, the oxygen partial pressure is controlled to simulate seeds within a water saturated anaroebic soil environment. However, other stress inducing atmospheres may be used. In this specification, the term "stress-inducing atmosphere" means an atmosphere that induces stress in seeds in a manner that permits reliable correlation to the stress induced in seeds by water soaked ground. It may be created by withdrawing oxygen with an oxygen scavenger as in the preferred embodiment but also by other means such as nitrogen purging or vacuum formation by container evacuation.

In a preferred embodiment of using the saturated cold germination kit, the aqueous solution soaked paper is placed at the bottom of the container base and the seeds are positioned on it. The moisture from the aqueous solution soaked paper and oxygen partial pressure in the kit is substantially uniform. The saturated cold germination test kit containing a high moisture content and a defined anaerobic environment may then be placed in a cold location for a designated period of time. After the conditioning period, a warm germination test is preferably performed to determine the viability and vigor of the seeds.

The saturated cold germination test kit uses single-walled components with a unitary body design. It provides a uniform reproducible gaseous and moisture test environment that provides a reproducible correlation with prior art test procedures but with greater standardization and reproducibility. In this specification, the term "saturated cold germination test kit" means a kit that is one of a multiple of substantially identical test kits designed for standardization and adapted to include features that permit it to provide a controlled moisture environment to seeds that reproducibly simulates the environment in which seeds are placed during cold and wet conditions such as occur during spring planting in some geographic locations. The controlled environment includes controlled moisture, oxygen and temperature conditions that stress the seeds and may provide an indication of the general vigor and viability characteristics and of the ability of the seeds to germinate if exposed to wet and cold growing conditions. The test may also be adapted to test for other stress conditions such as salinity which is useful in determining the ability of cotton seeds to germinate in wet, cold and high salinity conditions. In this specification, the words "test kit" does not imply that only seeds from one seed lot are being tested in one container although this is typically the procedure. Instead, several batches of seeds may be within one container to simplify some operations such as providing an anaerobic atmosphere. Individual batches within one container may be separately identified.

From the above description, it can be understood that the test kits of this invention and the methods of using and making them have several advantages, such as: (1) they are inexpensive to make such as by thermoforming, pressure forming or vacuum forming for example since they are formed of single thickness, inexpensive plastic or other formable sheet material; (2) because they are easily formed, they are disposable so they do not require reuse and thus decontamination between tests such as microbial decontamination; (3) the test parameters are more repeatable than currently practiced saturated cold germination test parameters; (4) the test results are more repeatable and may be correlated to other standard tests; (5) there are fewer steps; (6) it requires less time to perform the tests; and (7) it requires less labor to perform the tests.

BRIEF DESCRIPTION OF THE DRAWINGS

The above-noted and other features of the invention will be better understood from the following detailed description when considered with reference to the accompanying drawings, in which:

FIG. 3 is a perspective drawing of a test kit in accordance with an embodiment of the invention;

FIG. 4 is a perspective view of a container base forming a part of the embodiment of FIG. 3;

FIG. 5 is a fragmentary sectional view taken through lines 5-5 of FIG. 4;

FIG. 6 is a plan view of the container base of FIG. 4;

FIG. 7 is an elevational view of the container base of FIG. 4;

FIG. 8 is a perspective view of an insert or seed holder in accordance with an embodiment of the invention;

FIG. 9 is a plan view of a seed support used in the embodiment of FIG. 8;

FIG. 10 is an elevational view of the insert or seed holder of FIG. 8;

FIG. 11 is a plan view of the insert or seed holder of FIG. 8;

FIG. 12 is a perspective view of a lid usable in the kit of FIG. 4;

FIG. 13 is a plan view of the lid of FIG. 12;

FIG. 15 is a elevational view of a saturated cold germination test kit in accordance with an embodiment of the invention;

FIG. 16 is an exploded elevational view of the test kit of FIG. 15;

FIG. 17 is a perspective view of a container base usable in the embodiment of FIG. 15;

FIG. 18 is a fragmentary sectional view of the outer wall of the container base of FIG. 17 taken through lines 18-18 of FIG. 17

FIG. 19 is a perspective view of a container lid viewed from the inside of the lid usable in the test kit of FIG. 15;

FIG. 20 is a plan view of the lid of FIG. 17;

FIG. 21 is a fragmentary sectional view of the outer wall of the lid of FIG. 17 taken through lines 21-21 of FIG. 17;

FIG. 22 is a fragmentary sectional view of an elongated keeper section taken through lines 22-22 of FIG. 20;

FIG. 23 is a perspective view of a mounting plate of an oxygen scavenger holder usable in the embodiment of test kit of FIG. 15; and FIG. 24 is an elevational view of the mounting plate of an oxygen scavenger holder of FIG. 23.

DETAILED DESCRIPTION

Figures 1, 2:
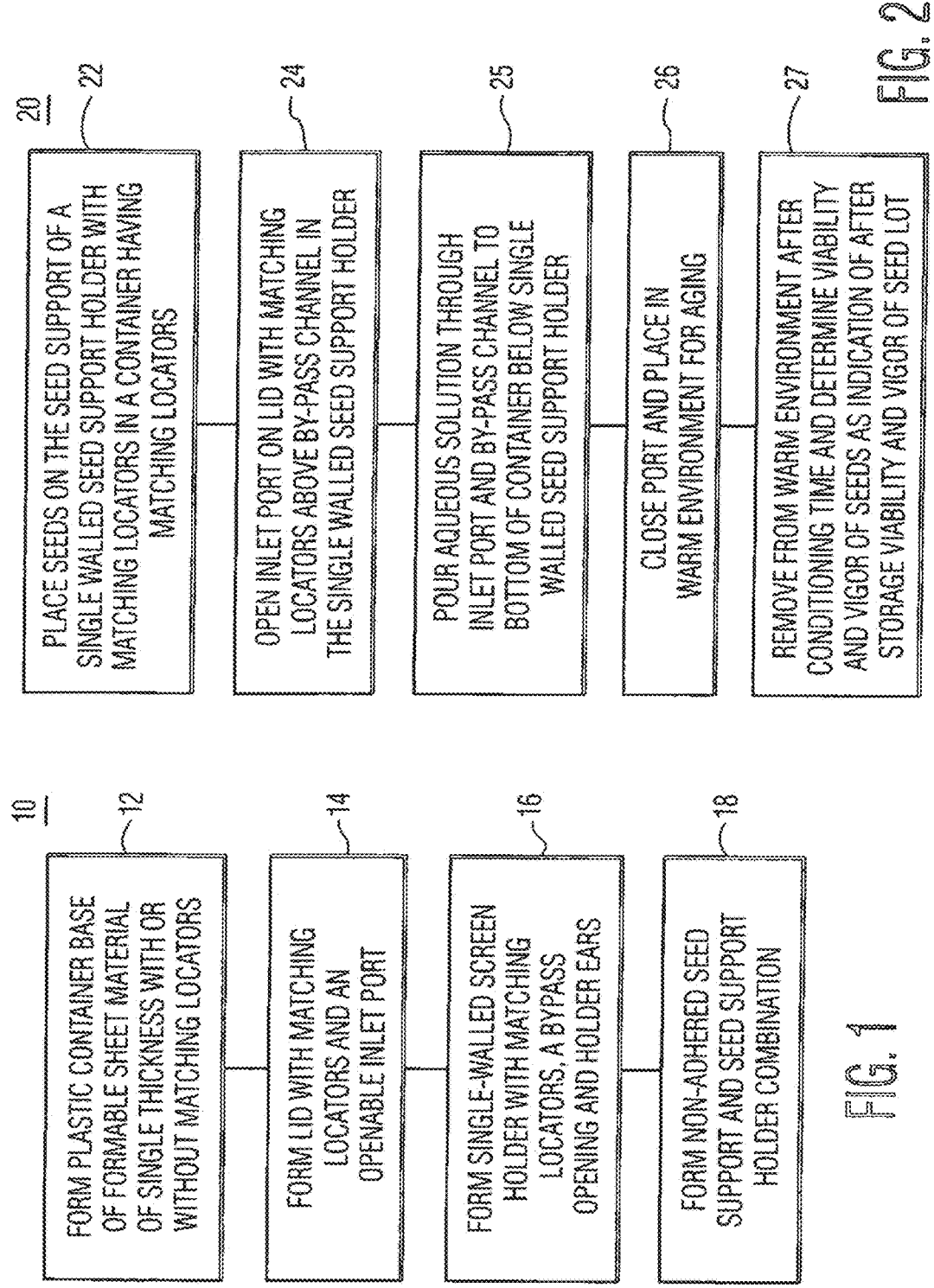
FIG. 1 is a flow diagram of a method of making a test kit in accordance with an embodiment of the invention.
FIG. 2 is a flow diagram of a test procedure in accordance with an embodiment of the invention.

In FIG. 1, there is shown a flow diagram 10 of a process of making a test kit in accordance with an embodiment of the invention having the step 12 of forming a container base of formable sheet material of single thickness with or without matching locators, the step 14 of forming a lid with matching locators and an openable inlet port, the step 16 of forming a single-walled seed support with matching locators, bypass opening and holder ears; and the step 18 of forming a non-adhered seed support and seed support holder combination. In this specification, the terms "matching locators" means markings and/or physical construction of parts that aid the parts in or force the parts to go together with a particular orientation with respect to the container. In this case, the lid has an openable port which must be aligned with a bypass opening in a seed holder within the container base beneath the lid and matching locators are used on the container base, the lid and the seed holder so that the openable port falls directly over the bypass opening to permit water or an aqueous solution to be poured through the openable port and flow underneath the seed holder.

In the preferred embodiment, the plastic is polyvinyl chloride but any other suitable formable sheet material may be used such as for example polyethylene, polylactic acid, polyacrylates, acrylonitrile butadiene styrene, polybutadiene and the like. Preferably, when the test kit is biodegradable, a biodegradable plastic such as polylactic acid is used in the test kit. The matching locators in the preferred embodiment are between the container base, the lid and between the container base and the single-walled seed support but could be between the lid and the single-walled seed support.

In this specification, the term "non-adhered seed support and seed support holder combination" means a seed support holder and seed support design in which the seed support is held in place without the use of an adhesive or heat sealing or softening plastic to embed the seed holder. Instead, the seed support is held in place by frictional forces and the tension caused by the stiffness of the seed support or the material holding the seed support. In the preferred embodiment, the seed support is a screen and the portions of the screen on four sides are bent to fit under upwardly bent portions of a screen holder while the main edge of the screen fits on a horizontal ledge.

In this specification, the term "a single-walled seed support holder" means a seed support formed of plastic or other suitable formable sheet material without walled portions extending transverse to the other wall portions other than an edge where the transverse wall portions are bent. In a single-walled seed support, the supporting horizontal walls that support the seed support are at the end or ends of wall portions to which they are transverse and are bent from substantially the same thickness of material. The seed support receives the seeds and is within and a part of the seed support holder. In the preferred embodiment, the seed support is a screen. All of the parts of the accelerated aging test kit are of a unitary body design. In this specification, the term "unitary body design" means a design in which strength is obtained by curved portions that increase the moment of inertia of a single thickness sheet rather than by either increasing the thickness of the sheet at locations where more strength is needed or by using reinforcing members at locations where strength is needed.

The process of FIG. 1 may also be used to make other test kits such as for example a saturated cold germination test kit. In the case of a saturated cold germination test kit, a unitary body designed container is made of an inexpensive plastic or other suitable formable sheet material. The plastic or other suitable formable sheet material may be a biodegradable plastic. The saturated cold germination test kit may be formed with an oxygen seal. A unitary construction cap may be formed and may include means for attaching the oxygen scavenger as will be described in more detail later. In the case of a saturated cold germination test kit, matching locators are not always needed because the orientations are not necessarily specific tabs on the lid and the base. However, in the preferred embodiment, a hinge on one side is used together with fasteners on another side to hold the lid in place and thus the lid and container base do have matching locators in the form of hinge parts and fasteners.

In FIG. 2, there is shown a flow diagram 20 of a process for performing accelerated aging tests on seeds comprising the step 22 of placing the seeds on a holder such as a screen of a single-walled seed support with matching locators that is within a container also having matching locators, the step 24 of opening the container lid's inlet port that is aligned by matching locators above a bypass channel in the single-walled seed support holder, the step 25 of pouring water or an aqueous solution through the opened inlet port and the bypass channel to the bottom of the container below the single-walled seed support holder, the step 26 of closing the inlet port and placing in a warm environment for accelerated aging, and the step 27 of removing the test kit from the warm environment after the conditioning time and examining the seeds for deterioration to obtain an indication of seed lot viability and vigor after storage. To measure the ability of the seed lot to be stored and to measure the quality of seeds withstanding accelerated aging, the seeds from the test kit may be tested in a standard warm germination test.

In FIG. 3, there is shown a simplified perspective view of a test kit 30 having a container base 32, a container lid 34, and four insert holding ears 38A-38D. The lid 34 has an inlet port closure 36. With this arrangement, an insert 60 (FIGS. 8, 10 and 11) may be placed into the test kit 30 and held in place by the insert holding ears 38A-38D.

In the embodiment of FIG. 3, the ears 38A-38D fit into slots in the container wall. The slots and ears serve as matching locators. In this specification, the term "matching locators" means markings on and/or physical construction of parts of the seed treatment kit that aid in or force the parts to go together with a particular correct orientation. These locators confine the lid 34 to a single orientation with respect to the container base 32 by their spacing along the wall so that the ears 38A-38D fit into the slots in only one orientation of the lid with respect to the container. However, the ears and slots could cooperate in other manners than in their location on the wall such as for example by having different width holding tabs or a different shaped container other than a square container to have unsymmetrical sides on both the lid and the container requiring the lid be put on in only one orientation. A tab 88 is designed to be flexible and may be pulled up to provide a port opening and snapped down onto the container side walls to close the port. A knob 89 is recessed in the tap 88 over the rim 50 (FIG. 4) to space the tap 88 from the rim and thus provide an easier grip to pull the tab up.

In FIG. 4, there is shown a perspective view of the container base 32 having an integrally formed bottom 42 and side walls 40A-40D formed of a single sheet of plastic or other formable sheet material to be able to retain a liquid. The integrally formed sheet of plastic or other formable sheet material is shaped into four integrally-formed downwardly recessed slots 52A-52D at the top of the corresponding side walls 40A-40D to receive corresponding ones of the insert holding ears 38A-38D (FIG. 3). These slots are not symmetrically located on the walls but are asymmetrical in a manner corresponding to the insert holding ears 38A-38D (FIG. 3) so that the insert holding ears 38A-38D (FIG. 3) can only fit into the slots 52A-52D when the insert is positioned exactly to correspond with the intended orientation of the container base 32 and container lid 34 (FIG. 3) with respect to each other. This orientation provides an opening for water or an aqueous solution of prescribed osmolarity such as a specified potassium chloride (KCl) solution to flow below the insert when poured through a port 54. Different solutions can be used to regulate the water partial vapor pressure. The properties of the solution are selected to accommodate the water potential objective of the test and species or variety being tested. Each of the slots 52A-52D ends in the flange 50 and has a corresponding cut-away portion 53A-53A shaped as a segment of a circle the flange 50 to permit easy grasping of the corresponding ears 38A-38D (FIG. 8) to lift the seed holder 60 (FIG. 8) or to insert it.

The three slots 52A, 52D and 52C are separated from each other by two corner stiffeners 46A and 46D formed in the side walls 40A, 40D and 40C. Slots 52B and 52C are separated from each other by port stiffeners 48A, 48B and 48C. The port stiffener 48C is a corner stiffener that is above the opening in the insert and positioned and shaped to receive a hollow portion of the port closure 36 (FIG. 3). A rim 50 extends all the way around the container base 32 and is formed at the end of the sheet of plastic or other formable sheet material being bent horizontally on a level with the bottom of the slots 52A-52D and port closure slots 44A and 44B. In FIG. 5, there is shown a fragmentary sectional view taken through lines 5-5 of FIG. 4 showing the side wall 40B bent over to form the corner stiffener 46B and bent horizontally at its very end to form the rim 50. With this arrangement, a stiffener which is of increased strength because of a higher moment of inertia is provided to receive the lid 34 (FIG. 3) and to accommodate slots for positioning and holding an insert.

In FIG. 6, there is shown a plan view of the container base 32 showing the position of the slots 52A-52D about the bottom of the container base 32 and of the corner stiffeners 46A, 46B, 46D and the port stiffeners 48A-48C illustrating the manner in which the lid 34 (FIG. 3) may be snapped onto the container base 32 only when properly oriented with the port 54 (FIGS. 3 and 4) properly aligned with a bypass channel. In the preferred embodiment, the container is square and has sides that are 4.94 inches long, a height of 1.65 inches from the outside bottom 42 to the top of the corner stiffeners 46A, 46B and 46D and port stiffeners 46A-48C. The slots 52A-52D are each 1.09 inches long and are positioned on the corresponding side walls 40A-40D (FIG. 4) to receive the corresponding one inch long insert holding ears 38A-38D (FIG. 3) only when the seed holder or insert 60 (not shown in FIG. 3 or 6; shown in FIGS. 8, 10 and 11) is positioned with the proper orientation with respect to the lid 34 (FIG. 3) and the container base 32. In the proper position, the bypass channel is under the port 54 (FIGS. 3 and 4).

To ensure that the seed holder or insert 60 (FIGS. 8, 10 and 11), the container base 32 (FIGS. 3, 4 and 6) and the lid 34 (FIGS. 3 and 8) are properly oriented, when put together, the insert 60, compartment or container base 32 and lid 34 are each asymmetrical in at least one respect but match each other so that they will only fit together when oriented so that the asymmetrical features of each are aligned. In the preferred embodiment, the insert holding ears 38A-38D (FIG. 3) and the compartment or container base slots 52A-52D are spaced so that the ears 38A-38D (FIG. 3) fit into the slots 52A-52D only when the seed holder 60 (FIGS. 8, 10 and 11) is properly positioned in the container base 32 because the holding ears 38A-38D (FIG. 3) and slots 52A-52D are asymmetrically located in the same manner and fit together in only one position. More specifically, the closest edge of the ear 38B (FIG. 3) to the closest corner of the angled wall section 74 (FIG. 8) of the container base is 1¾ inches and the closest edge of the ear 38C (FIG. 3) to its closest corner of an angled wall section 74 (FIG. 8) is 1¼ inches. The lid 34 (FIG. 3) is asymmetrical in that it has an upwardly extending opening 86 (FIG. 12) in only one corner and the compartment or container base 32 is asymmetrical in that it has an upwardly extending corner stiffener 48C of a unique size at only one corner, with the stiffener 48C matching the opening 86 (FIG. 12) in the lid 34. Since the lid 34 and container base 32 fit in only one orientation and the seed holder 60 and container base 32 fit in only one orientation, the seed holder 60 and lid 34 also fit with only one orientation.

In FIG. 7, there is shown an elevational view of the container base 32 viewing the side wall 40A. This FIG. illustrates: (1) the manner in which the slots 52A-52D with slot 52A as an example are recessed slightly to receive the insert holding ears 38A-38D (FIG. 3); (2) the manner in which the corner stiffeners 46A, 46B, 46D (FIG. 4) and the port stiffeners 48A-48C (FIG. 4) strengthen the container base 32 with the corner stiffeners 46A and 46B serving as examples; and (3) the manner in which the corner stiffeners 46A, 46B, 46D (FIG. 4) and the port stiffeners 48A-48C (FIG. 4) serve as guides and separators for the slots 52A-52D with the corner stiffeners 46A and 46B serving as examples.

In FIG. 8, there is shown a perspective view of an insert or seed holder 60 for the test kit 30 (FIG. 3) having four side walls 62A-62D respectively, four inner rim sections 64A-64D (only sections 64A, part of 64B and part of 64D being shown in FIG. 8) and a seed support or screen 66 closing the bottom of the insert 60. The inner rim sections 64A-64D are separated by raised rim portions 68A-68D (only 68A and 68B being shown in FIG. 8). The seed support or screen 66 lies on top of the inner rim sections 64A-64D except at the raised rim portions 68A-68D where it passes underneath so that the stiffness of the seed support tends to grip the inner rim sections 64A-64D and the raised rim portions 68A-68D.

At one corner of the four walls 62A-62D between the walls 62B and 62C, the walls meet at an angled wall section 74 instead of extending their entire length to a corner. The wall section 74 intersects the walls 62B and 62C at an angle to leave a space outside of the side walls between the insert 60 and the inner walls of the container base 32 (FIG. 4). The port closure 36 (FIG. 3) closes the container lid 34 over this empty spot to seal the port 54 (FIGS. 3 and 4). When the port closure 36 is opened, water or an aqueous solution may be poured from outside the container to bypass the insert through port 54. Thus, it serves as a by-pass channel.

To increase the friction holding the seed support 66 in place, seed support slots 70 (FIG. 9) are cut in the seed support 66 where the seed support 66 must pass through the walls of the raised portions 68A-68D to form seed support tabs 72 as shown in FIG. 9. The stiffness of the seed support members hold the seed support tabs 72 (FIG. 9) and the main seed support that overlies the inner rim sections 64A-64D together with tension exerting frictional force sufficient to keep the seed support 66 in place. The modulus of elasticity of the seed support members and the seed support 66 is sufficiently high to support seeds without the seed support 66 falling through the center of the rim. With this arrangement, the insert or seed holder 60 may be formed by pressure molding or pressure from any other suitable process to form a single uniform sheet of plastic or other formable sheet material and the seed support cut and inserted in place without the need for adhesives or the like, providing a simple inexpensive insert capable of supporting items such as seeds.

In FIG. 10, there is shown an elevational view of the insert or seed holder 60 showing insert holding ears 38A and 38C extending from the side walls 62A and 62C respectively (FIG. 8) with the center insert holding ear 38D extending from side wall 62D (FIG. 8). The raised rim portion 68D is shown on either side of the rim sections 64C and 64D receiving the seed support tabs 72 (FIG. 9) underneath it with the seed support 66 being above the rim sections 64C and 64D to be frictionally held by the rim sections and raised portions. As best shown in this view, the seed support 66 is held in place over the open bottom of the insert or seed holder 60 to be able to hold seeds.

In FIG. 11, there is shown a plan view of the insert or seed holder 60 more clearly showing the location of the insert holding ears 38A-38D, the raised portions 68A-68D of the rim and the lower inner rim sections 64A-64D with the seed support 66 covering the bottom and being held in place by friction with a portion of the seed support 66 resting on top of the lower inner rim sections 64A-64D and a portion being below the raised rim portion 68A-68D. With this arrangement, the stiff seed support 66 is held in place to support items on it.

In FIG. 12, there is shown a perspective view of the lid 34 having the port closure 36 and a container closure 80. The container closure 80 includes a central flat section 90, a wall 82 extending downwardly, perpendicular to the flat section 90, and an outwardly extending rim 92 parallel to the flat section 90 and extending around the lid up to the port closure 36. At the port closure 36, there is a longitudinal slot 84 opening upwardly to provide an angled location where the port closure 36 may be bent upwardly. Between the slot 84 and the corner, there is an opening 86 sized to snap over the port stiffener 48C (FIG. 4) of the container base 32.

The opening 86 is bounded by an outwardly extending tab 88. The slot 84 and opening 86 permit the port closure 36 to be bent upwardly away from the container to open the port 54 (FIGS. 3 and 4) and bent downwardly to permit the port to be closed so that the port stiffener 48C (FIG. 4) fits inside the opening 86 to form a relatively tight seal. In this manner, the entire lid 34 may be formed by thermoforming, vacuum forming or pressure molding from a single sheet of uniform thickness plastic or other formable sheet material. In FIG. 12, there is shown another perspective view of the lid 34 illustrating more clearly the outwardly extending tab 88, the longitudinal slot 84, and the hollow opening 86. As best shown in this arrangement, the tab 88 is formed to easily pull up the port closure 36 and open the port 54 and snap down to hold the port closure 36 in place and close the port 54.

In FIG. 13, there is shown a plan view of the lid 34 having the port closure 36 and the container closure 80. The container closure 80 includes the central flat portion 90, the side wall 82 and the rim 92. The side wall 82 extends downwardly from the flat portion 90 and ends in an integrally formed rim or flange 92 that extends outwardly from the perpendicular side wall 82. The flat portion 90, side wall 82 and rim or flange 92 end at one corner of the lid 34 which corner forms the port closure 36. The upwardly extending opening 86 and a downwardly extending groove 84 have a curved outer edge that engages the port stiffener 48C (FIG. 4) to hold the port closure 36 down when the port 54 (FIGS. 3 and 4) is closed. The port closure 36 bends about the downwardly extending groove 84, allowing for the opening and closure of the port closure 36 and thus, the opening and closure of port 54.

Figure 14:
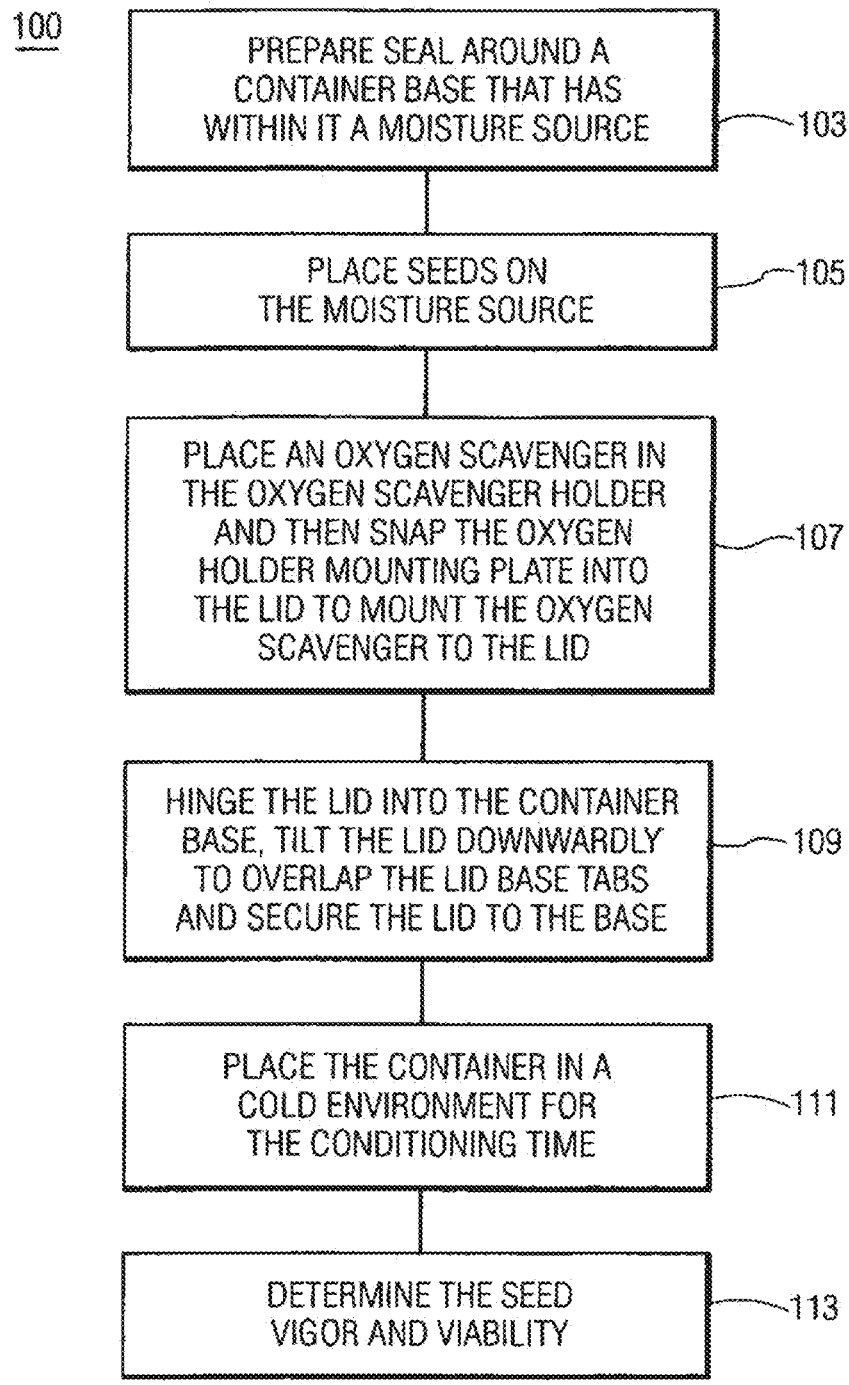
FIG. 14 is a flow diagram of a saturated cold germination test in accordance with an embodiment of the invention.

In FIG. 14, there is shown a flow diagram 100 of a process for saturated cold germination tests comprising the step 103 of preparing a seal around a container base that has within it a moisture source, the step 105 of placing seeds on the moisture source, the step 107 of placing an oxygen scavenger in the oxygen scavenger holder and then snapping the oxygen scavenger holder into the lid to mount the oxygen scavenger to the lid, the step 109 of hinging the lid into the container base, tilting the lid downwardly to overlap the lid and the base tabs and secure the lid to the base, the step 111 of placing the container in a cold environment for the conditioning period, and the step 113 of then assessing seed viability and vigor response through a warm germination test.

This procedure gives a measure of seed viability and vigor under stress conditions and particularly those that simulate early spring planting conditions in many crop production environments. After the conditioning period, seed viability and vigor are typically measured by a conventional warm seed germination test. While in the preferred embodiment, an anaerobic atmosphere is obtained by removing oxygen from the container, the test may be performed by using other stress inducing techniques such as by replacing the oxygen containing air with a nitrogen atmosphere or by creating a vacuum or partial vacuum in the container. In this specification, the word "hinge" as applied above to the base and lid of the saturated cold germination test kit means to fasten an edge of the base to an edge of the lid (referred to herein as "hinged edges") with a flexible connection that holds the two edges together while permitting the lid to swing closed and be held down to form a seal by one or more holders spaced from the edge.

In this specification, the term "saturated cold germination test kit" means a kit that is one of a multiple of substantially identical test kits designed for standardization and adapted to include features that permit it to provide a specific gas partial pressure and controlled moisture environment to seeds that reproducibly simulate the environment in which seeds are placed during cold and wet conditions such as occur during spring planting in some geographic locations or other stress conditions. Generally, the controlled environment includes controlled moisture, oxygen and temperature conditions that stress the seeds and provide an indication of the ability of the seeds to germinate and produce viable seedlings if exposed to similar conditions. In this specification, the term "stress-inducing atmosphere" means an atmosphere that induces stress in seeds in a manner that permits reliable correlation to the stress induced in seeds by cold water soaked ground. It may be created by withdrawing oxygen with an oxygen scavenger as in the preferred embodiment but also by other means such as nitrogen purging or vacuum formation.

In FIG. 15, there is shown an elevational view of a saturated cold germination test kit 102 having a container base 104 and a lid 106. Between the container base 104 and the lid 106, there is a substantially airtight seal, and within the container, there is a source of moisture and an oxygen scavenger that creates an anaerobic atmosphere to stress the seeds. In the preferred embodiment, the source of moisture is in the base and the oxygen scavenger is attached to the inside of the lid. In the prior art and in this saturated cold test protocol, the stress on the seeds is increased further by placing the test kit 102 in a cold location. In FIG. 15, a hinged edge 119 is shown, which hinged edge holds the lid 106 in engagement with the container base 104 at the hinged edge 119 with an airtight seal.

In FIG. 16, there is shown an exploded elevational view of the test kit 102 having the container base 104, a source of moisture 108, an oxygen scavenger mounting plate 110, an oxygen scavenger 112 and the lid 106. The source of moisture 108 in the preferred embodiment is a pack of paper soaked with water or an aqueous solution. A suitable commercial pack is sold by Seedburo Equipment Company under the trademark, KIMPAK. It is available from Seedburo Equipment Company, 1022 West Jackson Blvd., Chicago, Ill. 60607 or from Kamterter, L.L.C., 1035 North 33$^{rd}$ Street, Lincoln, Nebr. 68503 but any other suitable techniques for providing moisture or sources of moisture may be utilized. The KIMPAK germination paper is non-toxic paper toweling that is soaked in water or an aqueous solution and comes in several different sizes. In the preferred embodiment, the source of moisture 108 is put in the bottom of the container base 104 and seeds are located on top of it during a test, preferably with the seed germ downward into the paper. However, there are other ways of insuring that the germ is within adequate moisture than placing the germ downward into paper such as by covering or surrounding the seeds with a moist layer of paper or inert granular material.

The oxygen scavenger assembly 113 includes the mounting plate 110 for the oxygen scavenger assembly 113 and the oxygen absorbing pack 112 (sometimes referred to as an oxygen scavenger). The oxygen absorbing pack 112 may be any oxygen absorbing pack suitable for the purpose, many of which are commercially sold. In the preferred embodiment, the oxygen absorbing pack 112 is sold under the trademark, FRESHPAX, by MultiZorb Technologies, 325 Harlam Road, Buffalo, N.Y. In the embodiment of FIG. 16, the oxygen scavenger 112 is held attached to the lid 106 by the mounting plate 110 for an oxygen scavenger holder that includes mounting posts (not shown in FIG. 16; shown in FIGS. 19 and 20) in the lid 106. The posts serve as a fixed half of the oxygen scavenger assembly 113. However, the oxygen scavenger may be included within the kit 102 in any other manner that removes oxygen and thus creates a simulated anaerobic and fully controlled oxygen partial pressure environment reproducible test kit.

The container base 104 is formed of a single sheet of plastic or other formable sheet material in an inexpensive tooling system such as by a thermoforming system, a vacuum forming system or a pressure molding system. It includes around its periphery a liquid trough 114 (FIG. 17) formed of an upwardly opening curved wall that serves the purpose of providing stiffness and strength as a high moment of inertia frame as well as holding a liquid forming a gas exchange seal in the trough 114 (FIG. 17). With this arrangement, the engagement of the bottom of the lid 106 in the liquid trough 114 provides an airtight seal. The lid 106 contains multiple grooves 116 (FIG. 16) in a crisscross pattern to provide strength by providing a high moment of inertia for the thin walled plastic or other formable sheet material of which it is formed. It is also formed of a single sheet of plastic or other formable sheet material in an inexpensively tooled process such as by thermoforming, vacuum forming or pressure molding. Two snap fasteners 135A and 135B are formed at two corners on the side 121 (FIG. 17) formed of corresponding pairs of flexible snap ends 133A (FIG. 17), 137A (FIG. 19) and 133B (FIG. 17), 137B (FIG. 19).

In this specification, the term "snap fastener" means any fastener that holds parts together by enabling one or more members of the fastener to stretch or flex when force is exerted on it by a cooperating member and then to snap around a cooperating member or portion of the cooperating member with the result that the cooperating members impede the easy separation of the cooperating members. In the snap fasteners 135A and 135B of the preferred embodiment, the snap ends 133A and 133B (FIG. 17) of the tabs 120A and 120B respectively are flexed with the snap ends 137A and 137B (FIG. 19) of the tabs 150A and 150B so that the snap ends 137A and 137B (FIG. 19) of the lid 106 are beneath the snap ends 133A and 133B (FIG. 17) of the container base 104 and the portion of the tabs 150A and 150B other than the snap ends 137A and 137B are above the tabs 120A and 120B.

In FIG. 17, there is shown a perspective view of the container base 104 having a bottom 122, a side wall 130 and a trough 114. The side wall 130, the bottom 122 and the trough 114 are all formed from the same sheet of plastic or other formable sheet material and are integral with each other. The bottom 122 is square in shape in the preferred embodiment and the trough 114 forms its four side walls that extend upwardly from the bottom to form a container that when sealed to a lid is airtight. The trough 114 includes an integrally connected double inner side wall 132 and a trough outer wall 124 joined at the bottom with the space between the inner side wall 132, the bottom 122 and the trough outer wall 124 forming the trough 114 to hold a liquid. At the upper end of the trough 114, the outer wall 124 slants upwardly and outwardly to a flange 118 except that at a hinge side 119, there is an elongated keeper section 123 between the trough outer wall 124 and the flange 118. On opposite sides of the container base 104, the flange 118 is expanded into tabs 120A and 120B. On the inner side of the trough 114, the double ended side wall 132 includes a wall 126 slanting upwardly to a rounded top portion 128 and then a downwardly slanting side wall 130 that extends to the bottom 122. This construction is a unitary design that provides rigidity and strength from its high moment of inertia. Each of the tabs 120A and 120B have a corresponding one of the outwardly-extending flexible snap ends 133A and 133B forming one half of two corresponding ones of snap fasteners 135A and 135B (FIG. 16).

The hinge side 119 of the container base 104 is one half of a hinged edge. The hinged edge is opposite the side 121 that extends between the two tabs 120A and 120B and includes the outward extending elongated keeper section 123 extending from a location slightly less than one inch onto an adjacent side, across the entire length of side 119 to a location slightly less than one inch on the other adjacent side. The keeper section 123 extends outwardly approximately one thirty seconds of an inch and starts with a shoulder one eighth inch from the top of the rounded top portion 128 of the double wall 132.

In FIG. 18, there is shown a fragmentary sectional view of the trough outer wall 124, the elongated keeper section 123 and a flange 125 taken through lines 18-18 of FIG. 17. As shown in this view, the elongated keeper section 123 extends downwardly and outwardly at an acute angle from the vertical and includes an upper, outwardly-extending horizontal flange 125, a horizontal shoulder 129 that extends inwardly to the trough outer wall 124 and a bottom portion 131 of the trough 114 (FIG. 17). The elongated keeper section 123 forms a five-degree angle with the vertical. When the container base 104 (FIG. 17) is hinged to the lid 106 (FIG. 19), the flange 125 is a bottom flange of the hinged edge 119. The elongated keeper section 123, the shoulder 129, the trough outer wall 124 and the bottom 131 of the trough 114 are outside the corresponding parts of the edge of the lid 106 to which the container base 104 is hinged.

In FIG. 19, there is shown a perspective view of the lid 106 viewing it from the inside of the lid having a sealing wall 140 and a fixed half 136 of the oxygen scavenger holder. The sealing wall 140 fits within the liquid trough 114 (FIG. 17) where it, together with the liquid in the liquid trough, forms an airtight seal to permit oxygen to be removed from the test kit 102 (FIG. 16) by the oxygen scavenger 112 (FIG. 16). The fixed half 136 of the oxygen scavenger holder receives an oxygen scavenger holding plate 110 (not shown in FIG. 19; shown in FIGS. 16, 23 and 24) to form an open oxygen scavenger holder for holding an oxygen scavenger pad 112 (FIG. 16).

The sealing wall 140 includes a lower edge 144 (lower refers to its position when placed on top of the container base to close the container) with a first outer plastic sheet 156 (FIG. 21) extending upwardly and outwardly from the edge 144 to a shoulder 157 and an inner plastic sheet 154 extending upwardly to an inside surface 142 of the top of the lid 106. A second outer plastic sheet 146 on each side except hinge side 119 that extends upwardly and outwardly from the outer edge of the shoulder 157 to an outwardly extending horizontal flange 148 and on hinge side 119 is integral with a wall 146A (FIG. 22) that extends inwardly and upwardly to the flange 148. The flange 148 has two tabs 150A and 150B extending horizontally outwardly. The first outer plastic sheet 156 (FIG. 22) includes a plurality of indentations spaced-apart around its circumference, one of which is shown at 158. These provide additional stiffness to the plastic sheet and serve as spacers to keep the lid evenly spaced in the liquid trough 114 when the lid is fastened to the base. Similarly, the inner sheet 154 includes a plurality of indentations extending downwardly one of which is shown at 152 which adds stiffness to the inner plastic sheet 154 of the sealing wall 140. At the hinge side 119, there is an angled section 146A (FIG. 22) between the flange 148 and the shoulder 157.

To hold the oxygen scavenger 112 (FIG. 16) within the test kit 102 (FIG. 16), the inner top wall includes the fixed half 136 of the oxygen scavenger holder formed within it. The fixed half 136 of the oxygen scavenger holder has four mounting posts 160A-160D which receive the mounting plate 110 (FIG. 16) to form an open cage type arrangement to hold an oxygen scavenger pad 112 (FIG. 16).

In FIG. 20, there is shown a plan view of the lid 106 showing the outer wall 146 extending downwardly and the flange 148 with the top wall having a plurality of indentations, one being shown at 162. The side indentations 152 in the inner wall 154 (FIG. 19) are also shown overlapping onto the top to improve the stiffness and strength of the lid 106. The posts formed on the inside of the lid shown at 160A-160D in FIG. 19 are indentations on the outside of the lid of a cylindrical nature as shown in FIG. 20. With this arrangement, the lid 106 with the mounting posts 160A-160D may be formed of a single thin sheet of plastic with indentations to increase the moment of inertia and a sealing wall 140 (FIG. 19) formed of the folded-over plastic sheet to form an edge 144 (FIG. 19) that fits into the liquid trough 114 (FIG. 17) of the container.

In FIG. 21, there is shown a fragmentary sectional view taken through lines 21-21 of FIG. 17 having a bottom wall 144 of the edge of the lid, an upwardly extending wall 156, a shoulder 157, a vertical wall section 146 and the outwardly extending flange 148. In FIG. 22, there is shown a sectional view of the elongated keeper section 123 taken through lines 22-22 of FIG. 20 that is substantially identical with the section of wall shown in FIG. 21 that extends on all sides of the lid except for the hinge side 119 (FIG. 17). However, in the elongated keeper section 123, instead of the vertical wall 146, there is a wall section 146A that angles from the outer edge of the shoulder 157 to the inner end of the flange 148. The hinge side 119 (FIG. 17) of the container base cooperates with the hinge side 119 of the lid to hold down the hinge side 119 of the lid (FIG. 19). Either one of the snap fasteners 135A and 135B (FIG. 16) provide the other point of attachment between the lid 106 and container base 104 to hold the two together firmly together during use.

In FIG. 23, there is shown a perspective view of the mounting plate 110 of the oxygen scavenger holder for the oxygen scavenger pad 112 (FIG. 16) having an outer rim 170, side walls 172, an inner compartment rim 174 at the top of the side walls 172, and an open central area 176. The side walls 172 extend between the outer rim 170 and the inner rim 174 spacing the inner rim 174 from the outer rim 170 to form compartment sides to hold the oxygen scavenger pad 112 (FIG. 16). Four sockets 178A-178D are spaced about the outer rim 170 to receive the mounting posts 160A-160D (FIGS. 19 and 20) and hold the mounting plate 110 of the oxygen scavenger holder against the inner side of the lid 106 with the oxygen scavenger being exposed to the inside of the test kit through the opening 176. The mounting plate 110 may be formed of a single sheet of plastic with a square section cut out at 176 and the side walls 172, outer rim 170 and inner rim 174 formed by thermoforming, vacuum forming or pressure forming with the sockets 178A-178D being similarly pressed in the outer rim.

In FIG. 24, there is shown a side elevational view of the mounting plate 110 of the oxygen scavenger holder showing the sockets 178A-178D (only 178A and 178B being shown in FIG. 24) and the outer rim 170 in the manner it would be mounted against the inner side of the lid. Of course the holder may take many different shapes and be mounted in any different location within the test kit to serve the same function.

In use, a moisture source such as a paper pad that is soaked in water or an aqueous solution is placed in the bottom of the container base 104 and seeds are placed on it. While paper that has been soaked in the water or the aqueous solution is used in the preferred embodiment, many other materials can be used as a reservoir for water or an aqueous solution such as agarose, sponges and sponge-like materials, inert granular materials such as vermiculite or silica particles. Some inert granular particles can provide moisture from all directions around the seed to avoid any difference in the moisture uptake by the embryo due to the physical orientation of seeds. In one convenient embodiment, the seeds are placed on a soaked paper base and covered with a suitable granular material. In a preferred embodiment, the seed germ is placed directly against the paper or other moisture source. In the preferred embodiment, an oxygen scavenger is located inside the oxygen holder mounted to the lid and the lid is sealed against the bottom compartment.

The seal is completed or reinforced by filling the liquid trough with Newtonian, or a viscous or viscoelastic liquid or a semisolid or other malleable material that serves as an oxygen barrier. Viscoelastic or very viscous or semisolid materials aid in preserving the seal during handling of the test kit. The sealing edge of the lid is inserted into the trough either before or after the trough is filled with the oxygen barrier. The test kit is then located at a cold temperature for the conditioning period and the seeds examined after that period of time to assess their viability and vigor. The examination of the seeds usually includes a standard warm germination test to determine how many of the seeds will germinate normally after the conditioning period of the saturated cold germination test.

It has been found that this saturated cold germination test shows a close correlation with other standard saturated cold germination tests and may be used for comparison with seed lots tested by other saturated cold germination tests. The three types of stresses applied in the preferred embodiment are cool temperature, high moisture and reduced oxygen. These three types of stresses can be applied and controlled to provide an accelerated measure of the effect of planting in adverse conditions in a standardized and repeatable manner. These tests may be used for seed lot quality assessment.

From the above description, it can be understood that this saturated cold germination kit and method of using and making it have several advantages, such as: (1) the kit is inexpensive to make by pressure forming or thermoforming or vacuum forming since it is formed of single thickness, inexpensive plastic; (2) because it is easily formed, it is disposable and does not require decontamination between tests; (3) the tests results are more repeatable and may be correlated to or replace other standard tests; (4) there are fewer steps and less labor because standard kits are provided and thus the locating, gathering and assembly of components is not necessary; and (5) it requires less time because the test is shorter (e.g. protocol is seven days compared to ten).

Although a preferred embodiment of the invention has been described with some particularity, many modifications and variations in the invention are possible within the light of the above teachings. It is therefore to be understood that, within the scope of the appended claims, the invention may be practiced other than as specifically described.

What is claimed is:

1. A method of making a test kit comprising:
    forming a compartment of a single sheet of uniform thickness plastic, said compartment formed having a unitary body design;
    forming a lid having a moveable tab of a single sheet of formable sheet material to conform to the compartment; and
    forming an insert, said insert comprising at least one single-walled component,
    said at least one single-walled component being formed of a single sheet of formable sheet material.

2. The method of claim 1, wherein the step of forming an insert includes the substeps of forming a tube of formable sheet material, said tube of formable sheet material comprising one of an upper ledge and a lower ledge, a first ledge of said upper or lower ledges supporting said insert above a bottom of said compartment and a second ledge of said upper or lower ledges supporting a seed support, whereby a seed support holder is formed.

3. The method of claim 2, wherein the substep of forming a tube of formable sheet material comprises forming the upper ledge with one or more tabs, wherein said one or more tabs are supported from walls of a container, and forming the lower ledge to support the seed support.

4. The method of claim 3, wherein forming said lower ledge comprises forming a low ledge with elevated portions to support said seed support holder, and wherein forming said upper ledge comprises forming a top ledge with a horizontal flange to support the seed support.

5. The method of claim 1, in which the step of forming a lid comprises the step of forming a lid that includes the movable tab formed onto it with slots to permit bending, whereby said moveable tab may be lifted to provide an opening to access a bypass channel.

6. The method of claim 1, wherein the step of forming a lid having a moveable tab further comprises forming the moveable tab with or as a matching locator.

7. The method of claim 6, wherein forming the moveable tab with or as a matching locator further comprises forming one of a snap fastener and an openable inlet port.

8. The method of claim 1, wherein forming the compartment having a unitary body design comprises forming components of said compartment as components with curved portions that increase a strength and a moment of inertia of said component or said compartment.

* * * * *